(12) United States Patent
Engel et al.

(10) Patent No.: US 6,544,551 B1
(45) Date of Patent: Apr. 8, 2003

(54) SOLID PHARMACEUTICAL COMPOSITIONS CONTAINING HEXEDECYLPHOSPHOCHOLINE (MILTEFOSINE) FOR ORAL ADMINISTRATION IN THE TREATMENT OF LEISHMANIASIS

(75) Inventors: Juergen Engel, Alzenau (DE); Werner Sarlikiotis, Frankfurt (DE); Thomas Klenner, Ingelheim (DE); Peter Hilgard, Frankfurt (DE); Dieter Sauerbier, Werther (DE); Eckhard Milsmann, Bielefeld (DE)

(73) Assignee: Zentaris AG, Frankfurt am Main (DE)

( * ) Notice: Subject to any disclaimer, the term of this patent is extended or adjusted under 35 U.S.C. 154(b) by 0 days.

(21) Appl. No.: 09/624,890

(22) Filed: Jul. 24, 2000

Related U.S. Application Data

(63) Continuation of application No. PCT/EP98/00345, filed on Jan. 22, 1998.

(51) Int. Cl.$^7$ .............................. A61K 9/48; A61K 9/20
(52) U.S. Cl. ................. 424/451; 424/452; 424/456; 424/464; 424/465; 424/466
(58) Field of Search ............................. 424/451, 452, 424/456, 464, 465, 466

(56) References Cited

U.S. PATENT DOCUMENTS

| | | | |
|---|---|---|---|
| 4,762,658 A | 8/1988 | Rothfuss et al. ............ 264/122 |
| 4,837,023 A * | 6/1989 | Eibl ............................ 424/439 |

FOREIGN PATENT DOCUMENTS

| | | |
|---|---|---|
| DE | 888 444 C | 11/1952 |
| EP | 0 419 998 A | 4/1991 |
| EP | 0 534 445 | 3/1993 |
| EP | 534445 A1 * | 3/1993 |

OTHER PUBLICATIONS

Arias, Jorge R.PhD, Monteiro, Pedro S., and Zicker, Fabio, MD PhD, Emerging Infectious Diseases, vol. 2, No. 2—Apr.–Jun. 1996.*

* cited by examiner

Primary Examiner—Thurman K. Page
Assistant Examiner—Rachel M. Bennett
(74) Attorney, Agent, or Firm—Oblon, Spivak, McClelland, Maier & Neustadt, P.C.

(57) ABSTRACT

The present invention relates to new solid pharmaceutical compositions containing hexadecylphosphocholine (miltefosine) for oral administration in the treatment of leishmaniasis, a process for the manufacture of said pharmaceutical composition, a dosage scheme for oral administration of said pharmaceutical composition in the treatment of leishmaniasis, and finally a combination comprising said solid pharmaceutical composition, antiemeticum, and/or an antidiarrhoeal.

23 Claims, No Drawings

US 6,544,551 B1

SOLID PHARMACEUTICAL COMPOSITIONS CONTAINING HEXEDECYLPHOSPHOCHOLINE (MILTEFOSINE) FOR ORAL ADMINISTRATION IN THE TREATMENT OF LEISHMANIASIS

CROSS-REFERENCE TO RELATED APPLICATIONS

This Application is a continuation of PCT/EP98/00345, filed Jan. 22, 1998, the entire content of which is hereby incorporated by reference.

BACKGROUND OF THE INVENTION

1. Field of the Invention

The present invention relates to new solid pharmaceutical compositions containing hexedecylphosphocholine (miltefosine) for oral administration for the treatment of leishmaniasis. These compositions have suitable flowability for processing into forms such as tablets and have a purity suitable for oral administration for treatment of leishmaniasis. Other aspects of the invention include compositions comprising the new solid pharmaceutical miltefosine composition, an antiemeticum, and/or an antidiarrhoeal product; methods of, and dosage schemes for oral administration of said pharmaceutical composition in the treatment of leishmaniasis; and processes for the manufacture of solid pharmaceutical compositions containing miltefosine.

2. Background of the Invention

Leishmaniasis is a name for a group of tropical diseases which are caused by flagellates of the genus Leishmania. Leishmaniasis is transmitted by various blood-sucking insects. The manifestations of leishmaniasis may be visceral (e.g. kala-azar), mucocutaneous (e.g American leishmaniasis) or cutaneous (e.g Aleppo boil or diffuse cutaneous leishmaniasis). The incubation period for leishmaniasis is weeks or months. A very high mortality rate is observed in untreated cases, particular in instances of kala-azar and American leishmaniasis.

Leishmania is a parasitic disease which is often encountered in geographical areas with extreme tropical climates and where medical care is complicated by inadequate modes of transport. Medications and methods for treating leishmaniasis must take into account these harsh environmental conditions and constraints.

Prior to the present invention there was no medicament available for oral therapy of leishmaniasis. Prior art therapies for leishmaniasis required intravenous (i.v.) injection of agents such as pentavalent antimony compounds (e.g. sodium stibogluconate) and aromatic diamidines. However, such methods cause severe side-effects due to the high toxicity of the prior art medications. Further, i.v. administration of such medications increases the risk of infection compared to medications which are administered orally or topically. Additionally, the prior art methods are inconvenient, particularly in tropical countries without adequate transportation, adequate hospital care facilities or adequate medical resources.

The usability of milefosine for oral and topical treatment of leishmaniasishas been described by Eibl et al. in German unexamined patent application no. P 41 32 344, filed Sep. 27, 1991. However, miltefosine is difficult to handle due to its poor flowability, its hygroscopicity and its ability to become electrostatically charged.

One reason miltefosine has poor flowability is because of its high hygroscopicity. The incorporation of water molecules into miltefosine may result in an increase in weight of up to 30%, melting point depression, or in agglomeration and agglutination of the crystals. Miltefosine which contains water exhibits insufficient workability to be further processed into solid pharmaceutical compositions, such as tablets, capsules or sachets. Flowability is desirable and one of the essential prerequisites for manufacturing solid pharmaceutical compositions on an industrial scale, however, the flowability of water-containing miltefosine is particularly insufficient for these purposes.

While miltefosine may be obtained in dry or anhydrous form as crystalline plates with a definite melting point of above 200° C., this form has the undesirable characteristic of becoming electrostatically charged. Anhydrous miltefosine exhibits inadequate flowability for processing into a solid pharmaceutical composition due to its significant tendency for electrostatic charging, particularly when stirred in dry state. Moreover, electrostatic charging raises significant safety concerns due to the risks of both explosion during processing or handling. Electrostatic charging may also cause damage to electronic parts in machinery which dry miltefosine comes into contact during its handling and processing.

Prior art attempts to overcome these problems have been unsatisfactory because they rely on processes which use highly volatile and toxic halogenated hydrocarbons that can introduce undesirable contaminants into the final products. For example, Eibl et al. attempt to overcome the aforementioned problems in the preparation of solid pharmaceutical compositions containing miltefosine by means of a process which uses halogenated hydrocarbons. Eibl et al. suggest coating miltefosine onto the surface of silicon dioxide particles by making a suspension of 1 part by weight of silicon dioxide in a solution containing 1 part by weight of miltefosine and evaporating to dryness. While under laboratory conditions, the resulting solid dispersion exhibits sufficient flowability to be filled into capsules, the process as described by Eibl et al. requires the use of non-inflammable solvents which are highly volatile. The solvents used must be non-inflammable due to the danger of electrostatic charging. For all practical purposes, there are only two solvents available in the state of the art which meet these requirements, namely methylene chloride and chloroform. Both of these solvents are halogenated hydrocarbons and are classified as toxic and cancerogenic compounds, particularly chloroform. Halogenated hydrocarbons when ingested accumulate or are enriched in the fat tissues of animals and are only slowly metabolized. Therefore, solid pharmaceutical compositions containing miltefosine produced by the process of Eibl et al. which require the use of solvents like chloroform or methylene chloride suffer from the risk of contamination with these toxic compounds. Such compositions face a lengthy and costly regulatory process and may be denied regulatory approval for use in humans or in animals forming part of the food chain. Such risks discourage scaling up the prior art processes for industrial use.

Accordingly, there is a long-felt need for a solid pharmaceutical composition containing miltefosine having suitable flowability and purity, and which does not suffer from the health, regulatory and commercial risks associated with miltefosine produced by prior art processes.

BRIEF SUMMARY OF THE INVENTION

The present invention provides novel methods for manufacturing, processing or providing hexedecylphosphocholine (miltefosine) in a solid form having suitable flowability and purity for production of pharmaceutical compositions which do not suffer from the risks associated with miltefosine produced by prior art processes. These solid compositions are suitable and convenient for oral administration of miltefosine in the treatment of leishmaniasis. These compositions may be compound in a variety of forms and may contain other active ingredients such as an antiemeticum and/or an antidiarrhoeal product. Novel methods of treatment and dosage schemes using these new orally administered miltefosine compositions also form important aspects of the invention.

DETAILED DESCRIPTION OF THE INVENTION.

As noted above, prior art miltefosine products suffer from a number of problems. Surprisingly and unexpectedly, it has now been found that the aforementioned problems can be solved by simple physical mixing of miltefosine (HPC); at least one flowability-controlling agent and/or lubricant such as those selected from the group consisting of highly dispersed silicon dioxide, talc, magnesium stearate and mixtures thereof; and at least one filler, such as fillers selected from the group consisting of lactose, microcrystalline cellulose and mixtures thereof.

The subject matter of the present invention is new and non-obvious over the prior art since it is not necessary to use carrier particles or granulating solvents to.obtain a solid miltefosine-containing pharmaceutical composition with sufficient flowability. The present invention uses simple physical blending of miltefosine, a flowability-controlling agent and/or lubricant, and at least one filler, to provide a solid pharmaceutical blend having sufficient flowability to be further processed into forms such as capsules, tablets or sachets.

In contrast, according to the teaching of Eibl et al., the ordinary skilled person would have tried to achieve the desired flowability either by way of granules by using a granulating solvent other than water (due to the hygroscopicity of miltefosine) or by way of solid dispersions which require a large excess of silica gel.

In a preferred embodiment, the solid pharmaceutical composition according to the present invention can be filled into capsules, preferably hard gelatine capsules, pressed into tablets or effervescent tablets, or filled into sachets as a drinkable blend or effervescent blend.

The content of miltefosine per dosage unit is in the range of 10 to 800 mg, preferably in the range of 10 to 500 mg, more preferably in the range of 50 to 250 mg. The most preferred content is in the range of 50 to 150 mg. These ranges include all specific values and subranges there between, such as 10, 50, 250, 500, etc.

Suitable flowability-controlling agents include highly dispersed or colloidal silicon dioxide (e.g. Aerosil® such as Aerosil(® V200; DEGUSSA AG, Germany), magnesium stearate, talcum, talcum siliconisatum, calcium arachinate, cetyl alcohol, myristyl alcohol, and mixtures thereof. Lubricants that may be used include magnesium stearate or other stearates like calcium stearate, D,L-Leucine, talcum, stearic acid, lauric acid, polyglycols (mean molecular weight 3,000–35,000), fatty alcohols or waxes.

The preferred ratio between miltefosine and a flowability-controlling agent and/or lubricant is 1 part by weight of miltefosine to 0.01–0.6 parts by weight of the flowability-controller.

Anti-adhesion agents that may be used include for example: glycols, starch, talcum, talcum siliconisatum, aluminium stearate, stearic acid, magnesium stearate, calcium stearate or D, L-leucine.

Some examples of suitable flow-controlling agents, lubricants and antiadhesion agents are listed in the following textbooks:

W. A. Ritschel, DIE TABLETTE, Editio Cantor Verlag, page 125, 1st edition (1966);

Sucker, Fuchs, Speiser, PHARMAZEUTISCHE TECHNOLOGIE, g. Thieme Verlag, Stuttgart, pages 334 to 336, 1rst edition (1978);

Münzel, Büchli, Schultz, GALENISCHES PRAKTIKUM, Wissenschaftliche Verlagsanstalt, Stuttgart, page 731, 1rst edition, (1959);

R. Voigt, LEHRBUCH DER PHARMAZEUTISCHEN TECH NOLOGIE, 4th edition, Verlag Chemie, Weinheim, page 195, 1rst edition (1982);

P. H. List, ARZNEIMITTELLEHRE, Wissenschaftliche Verlagsanstalt, Stuttgart, page 86, 1rst edition (1976).

The solid pharmaceutical compositions according to the invention may also contain binding agents such as gelatine, cellulose, cellulose ethers, amyloses, dextrose, polyglycols, tragacanth., pectins, alginates, and/or polyvinylpyrrolidone.

The solid pharmaceutical compositions according to the invention may also contain disintegrating agents such as for example: starches (e.g. corn starch), modified starch (e.g. sodium starch glycolate, starch 1500), pectins, betonite, cellulose, cellulose derivatives (e.g. carboxymethyl celluloses), alginates, polyvinyl pyrrolidones, ultraamylopectin, cross-linked polyvinyl pyrrolidone or crosslinked carboxymethyl cellulose (Ac-Di-Sol/FMC).

Suitable fillers include lactose (e.g., spray-dried lactose), glucose, fructose, calcium phosphates, calcium sulfates, calcium carbonates, starch, modified starch, sugar alcohols such as sorbitol or mannitol, cellulose derivatives, saccharose, microcrystalline cellulose, and mixtures thereof. The preferred ratio between miltefosine and the filter is 1 part by weight of miltefosine to 0.1–120 parts by weight of the filler.

According to a further aspect of the invention, a process for the manufacture of the pharmaceutical composition according to the present invention is provided, comprising the steps of:

(a) blending miltefosine, the flow-controlling agent and the filler, optionally together with further auxiliary agents, thereby obtaining a pharmaceutical composition having sufficient flowability, and (b) filling the blend obtained into capsules or sachets, or alternatively, compressing the blend obtained into tablets.

The production of an oral pharmaceutical composition according to the present invention can be carried out by blending, mixing or homogenizing miltefosine with the usual physiologically tolerated fillings or fillers, carriers, dilutants and/or auxiliary substances at temperatures between 20 and 120° C. If desired such blends or mixtures can be used to prepare formulations which contain 10 to 800 mg of miltefosine in one dosage unit. The mixture thus obtained is poured into hollow cells of an appropriate size or filled into capsules of an appropriate size or granulated and then pressed into tablets, if desired, with addition of further common auxiliary substances. The active substance can for example be mixed with one or several of the following auxiliary substances: starch, cellulose, lactose, formalin-casein, modified starch, magnesium stearate, calcium hydrogenphosphate, highly-dispersed silicic acid, talcum and phenoxyethanol. If desired, the obtained mixture may be granulated with an aqueous solution containing for example gelatin, starch, polyvinyl pyrrolidone, vinylpyrrolidon-vinyl acetate copolymerisate or/and polyoxyethylene sobianmonooleate, as constituents. If desired such a granulate may be homogenized with one or several of the aforementioned auxiliary substances. Subsequently this mixture can be pressed into tablets or filled into into capsules whereby the tablets or capsules each contain 10 to 800 mg of miltefosine in one dosage unit.

The manufacture of the capsules and tablets occurs for example between 15° C. and 26° C., preferably between 18° C. and 22° C. The relative humidity in the production rooms should preferably not exceed 40%.

The preparation of the solid pharmaceutical compositions according to the invention is effected in a conventional manner, it also being possible to use conventional and customary pharmaceutical auxiliary substances and other conventional carriers and diluents. Miltefosine blends or mixtures can be melted or dissolved with a liquid and if required the moist compound can then passed through a strainer. As necessary, additional processing steps such as screening, drying and mixing with further excipients as well as filling in sachets or capsules, or compression into tablets are performed. Miltefosine containing blends can also be compounded or extruded according to the prior art to obtain a granulate.

According to the invention, the process for manufacturing the pharmaceutical compositions may further comprise the step of granulating the composition having sufficient flowability as obtained according to step (a) prior to step (b). Granulation can be effected according to methods known in the art, see e.g. *Hagers Handbuch der pharmazeutischen Praxis*, 5th edition, Springer Verlag, pages 722–742 (1991).

Examples of carriers and excipients that may be considered are those which are recommended or quoted in the following literature references as auxiliary substances for pharmacy, cosmetics and related fields: *"Ullmanns Encyklopädie der technischen Chemie"*, Volume 4 (1953), pages 1 to 39; *Journal of Pharmaceutical Sciences*, Volume 52 (1963), page 918 et seq.; *"H.v.Czetsch-Lindenwald, Hilfsstoffe für Pharmazie und angrenzende Gebiete"*; Pharm. Ind. issue 2 (1961), page 72 et seq.; Dr. H. P. Fiedler, "Lexikon der Hilfsstoffe für Pharmazie, Kosmetik und angrenzende Gebiete", Cantor K G, Aulendorf in Württemberg (1981).

Examples thereof are gelatine, natural sugars such as unrefined sugar or lactose, lecithin, pectin starches (e.g. corn starch), cyclodextrines and cyclodextrine derivates, polyvinyl pyrrolidone, polyvinyl acetate, gelatine, gum arabic, alginic acid tylose, talcum, lycopodium, silica gel (e.g. colloidal), cellulose, cellulose derivates (e.g. cellulose ether in which the cellulose hydroxy groups are partially etherified with lower saturated aliphatic alcohols and/or lower saturated aliphatic oxyalcohols, for example methyloxypropyl cellulose, methyl cellulose, hydroxypropylmethyl cellulose, hydroxypropylmethyl cellulose phthalate); fatty acids as well as magnesium, calcium or aluminium salts of fatty acids with 12 to 22 carbon atoms, in particular.saturated ones (e.g. stearates), emulsifiers, oils and fats, in particular vegetable fats (e.g. peanut oil, castor oil, olive oil, sesame oil, cottonseed oil, corn oil, wheat germ oil, sunflower seed oil, cod liver oil), in each case also including hydrogenated fats; mono-, di- and triglycerides of saturated fatty acid $C_{12}H_{24}O_2$ to $C_{18}H_{36}O_2$ and their mixtures, pharmaceutically acceptable single or multivalent alcohols and polyglycols such as polyethylene glycols as well as derivates thereof, esters of aliphatic saturated or unsaturated fatty acids (2 to 22 carbon atoms, in particular 10–18 carbon atoms) with monovalent aliphatic alcohols (1 to 20 carbon atoms) or multivalent alcohols such as glycols, glycerine, diethylene glycol, penteerythritol, sorbitol, mannitol and so on, which may optionally also be etherified, esters of citric acid with primary alcohols, acetic acid, benzylbenzoate, dioxolanes, glycerine formais, tetrahydrofurfuryl alcohol, polyglycol ether with $C_1$–$C_{12}$-alcohols, dimethylacetamide, lactamides, lactates, ethyl carbonates, silicons (in particular medium-viscous polydimethylsiloxanes), calcium carbonate, sodium, carbonate, calcium phosphate, sodium phosphate, magnesium carbonate and the like.

Other excipients that may be used are substances which aid disintegration (so called disintegrants) such as: cross-linked polyvinyl pyrrolidone, sodium carboyxmethyl starch, sodium carboxymethyl cellulose or microcristalline cellulose.

Powders are manufactured in the following manner: miltefosine, at least one flowability-controlling agent and/or lubricant, at least one filler, and optionally a flavouring agent and/or sweetener are blended and filled into sachets (bags) of the appropriate dosage unit. For use, the whole content of a bag, or alternatively a part of it, are stirred into water or fruit juice and then swallowed. This method makes it easy to administer or apply any level of dosage by the peroral route.

To prepare an effervescent tablet or an effervescent blend, miltefosine, at least one flowability-controlling agent and/or lubricant, and at least one filler are blended in conventional manner with a carbonate or an acid component. The blend obtained is pressed into tablets or filled into bags which also contain the complementary acid (when a carbonate blend is used) or carbonate (when a blend containing an acid component is used) components, as well as other flow-controlling agents and lubricants. Such effervescent tablets or blends may optionally contain flavourings. Administration of such products is performed by taking the tablet or blend in water.

The solid pharmaceutical compositions according to the invention may also contain flavoring, sweetening and/or aromatic substances. Aromatic substances may be selected from the following group of flavors: pineapple, apple, apricot, raspberry, cherry, cola, orange, passion fruit, lemon, grapefruit, vanilla, and chocolate. The following substances may be used as sweeteners: saccharin and its sodium salt, cyclamic acid and its sodium salt, ammonium glycyrrhizinate, fructose, xylitol, sorbitol, mannitol, aspartame, and acesulfam-K.

The effervescent powder or chewable or effervescent tablets are prepared using conventional processes as described in the literature, e.g. in the standard reference work by Sucker, Fuchs, and Speiser (ed.), Pharmazeutische Technologie, Thieme Verlag, Stuttgart). The preparation (all steps apart from drying) is carried out, for example, at temperatures between 10° C. and 80° C., preferably 18° C. to 50° C., in particular 20° C. to 30° C.

The production of miltefosine (hexadecylphosphocholine) is described in detail in the examples for hexadecylphosphocholine (miltefosine) as described in the German unexamined patent application no. P 41 32 344. Further methods for the production and purification of miltefosine are described, for example, in German unexamined patent applications nos. DE-A 27 52 125, DE-A 36 41 379, DE-A 36 41 491, DE-A 40 13 632, DE-A 36 41 377, the literature cited in these or in earlier patent applications or patent specifications is hereby incorporated by reference.

According to a further aspect of the present invention, a dosage scheme for the treatment of leishmaniasis in humans by oral administration of the pharmaceutical composition according to the present invention is provided.

In a preferred embodiment of the invention, the following dosage scheme in the treatment of leishmania in humans by oral administration is suitable:

Total daily dosage: 10–250 mg, preferably 50–150 mg a.i. miltefosine (a.i.=active ingredient);

Single or multiple daily dosage: a total daily dosage of 10–50 mg a.i. is preferably administered as a single daily dosage; a dosage between 50–250 mg a.i., preferably between 50–150 mg a.i. is administered orally as a multiple daily dosage, preferably as a twice daily dosage (100 mg a.i. total daily dosage) or three times daily dosage (150 mg a.i. total daily dosage). With regard to patient compliance, a 4–5 times divided daily dosage is generally regarded as an upper limit. Other dosages besides a 1–5 times divided daily dose, may also be used to facilitate cure of leishmaniasis.

In a preferred embodiment, multiple daily doses are administered in equal portions (e.g. 100 mg a.i./day=2×50 mg a.i./day or 150 mg a.i./day=3×50 mg a.i./day). These dosages are administered for a period of time of therapy of about 2–6 weeks, preferably 4 weeks.

According to a further aspect of the invention, a dosage scheme for the treatment of leishmaniasis in mammals other than humans by oral administration of the pharmaceutical composition according to the present invention is provided.

All mammals can be treated by the invention, for example, pets or small companion animals such as cats, dogs, ferrets, hamsters and other rodents. The treatment can be performed in the natural surroundings of the animals or in selected surroundings like animal hospitals or veterinary offices, with the former being preferred. All leishmania species can be treated by the inventive dosage scheme, especially *Leishmania major* and *Leishmania infantum*.

According to the dosage scheme of the invention, the total daily dosage in the treatment by oral administration is in the range of 1–15 mg a.i. miltefosine per kg body weight of the animal (mg a.i./kg). In a preferred embodiment, therapy is started with an initial total single dosage (loading dosage) in the range of 3–15, preferably 5–10 mg a.i./kg, and thereafter continued with a total daily dosage (maintenance dosage) in the range of 1–10, preferably 3–5 mg a.i./kg. The period of time for treatment is in the range of 2–8 weeks, preferably 4–5 weeks.

The solid miltefosine compositions of the invention may also be used as prophylactic agents against leishmaniasis and other diseases, either alone or in combination with other active ingredients.

According to a further aspect of the invention, solid miltefosine compositions may be combined with other active ingredients that provide relief of symptoms associated with disease or for a broader spectrum of treatment against leishmaniasis and other coincidental diseases. For instance, a combination of the pharmaceutical composition according to the invention with an antiemeticum and/or antidiarrhoeal for oral administration in the treatment of leishmaniasis is provided.

In a preferred embodiment of the invention, the pharmaceutical composition according to the invention is administered in combination with an antiemeticum and/or an antidiarrhoeal. The administration can be performed simultaneously or subsequently. The antiemeticum and the antidiarrhoeal can be administered independently of each other. The antiemeticum and/or antidiarrhoeal can either be contained in the pharmaceutical composition according to the invention or be contained in an pharmaceutical formulation independent thereof.

Suitable antiemetica are, for example, 5-HT3-receptor antagonists, substituted benzamides, corticosteroids, antihistaminica, neuroleptica of the phenothiatine-type, neuroleptica of the butyrophenone-type, benzodiazepines and cannabinoids. Preferred antiemetica are, inter alia, metoclopramid, domperidon and alizaprid.

Suitable antidiarrhoeal products are, inter alia, the opioids, such as loperamid.

The solid oral pharmaceutical compositions according to the invention are preferably useful in the treatment of leishmaniasis. However, other protozoal diseases, such as malaria, trypanosomiasis, toxoplasmosis, babesiosis, amoebic dysentery and lambliasis may also be treated using the agents or compositions according to the present invention. The agents or compositions according to the present invention are particularly suitable for those diseases in which the pathogen is present in inner organs such as the liver, spleen or kidney, in lymph knotes, bone marrow, and blood.

It is intended to elucidate the invention further by the following examples without the invention being restricted by these examples.

I. EXAMPLE FOR SOLID ORAL PHARMACEUTICAL FORMULATIONS ACCORDING TO THE INVENTION

Example 1

Hard Gelatine Capsule

Content: 10 mg miltefosine (hexadecylphocholine).

100 g miltefosine (hexadecylphosphocholine), 808.50 g lactose, 448.50 g microcrystalline cellulose, 26 g talcum and 13 g highly dispersed silicon dioxide are passed through a sieve with a mesh number of 0.8 mm and then are homogenized in a suitable mixer over 30 minutes. Then 4 g magnesium stearate (0.8 mm sieve) is added and the components are blended over further 5 minutes. The obtained mixture is filled in a known way in portions of 140 mg into gelatin hard capsules of 50 mg weight by using a suitable capsules machine.

Each capsule as obtained (total weight: 190 mg) hexadecylphosphocholine contains 10 mg.

The ratio between hexadecylphosphocholine: flowability-controlling agent/surfactant fillers in the filling mixture is 1:0.4, 12.4 (parts by weight).

Example 2

Hard Gelatine Capsule

Content: 50 mg miltefosine (hexadecylphocholine).

258 g hexadecylphosphocholine, 430 g lactose, 241 g microcrystalline cellulose, 14 g talcum, 7 g highly dispersed silicon dioxide and 2 g magnesium stearate were blended according to the process as described in Example 1. The thus obtained filling mixture is filled in portions of 185 mg into gelatine hard capsules of 59 mg weight in a known way by using a suitable capsules machine.

Each capsule as obtained (total weight: 244 mg) contains 50 mg hexadecylphosphocholine. The ratio between hexadecylphosphocholine—flowability-controlling agents and lubricants—fillers in the filling mixture is 1:0.09:2.6 (parts by weight).

Example 3

Hard Gelatine Capsule

Content: 100 mg miltefosine (hexadecylphosphocholine).

1000 g hexadecylphosphocholine, 584 g lactose, 345 g microcrystalline cellulose, 50 g talcum, 15 g highly dispersed silicon dioxide and 6 g magnesium stearate were blended according to the process as described in Example 1.

The thus obtained filling mixture is filled in portions of 200 mg into gelatin hard capsules of 76 mg weight in a known way by using a suitable capsules machine.

Each capsule as obtained (total weight: 276 mg) contains 100 mg hexadecylphosphocholine. The ratio between hexadecylphosphocholine: flowability-controlling agent: fillers in the filling mixture is 1:0.07:0.9 (parts by weight).

Example 4

Hard Gelatine Capsule

Content: 150 mg miltefosine (hexadecylphosphocholine).

150 g hexadecylphosphocholine, 30 g lactose, 15 g microcrystalline cellulose, 3 g talcum, 2 g highly dispersed silicon dioxide and 1 g magnesium stearate were blended according to the process as described in Example 1. The thus obtained filling mixture is filled in portions of 201 mg into gelatin hard capsules of 76 mg weight in a known way by using a suitable capsules machine.

Each capsule as obtained (total weight: 277 mg) contains 150 mg hexadecylphosphocholine. The ratio between hexadecylphosphocholine: flowability-controlling agent: fillers in the filling mixture is 1:0.04:0.3 (parts by weight).

Example 5

Hard Gelatine Capsule

Content: 200 mg miltefosine (hexadecylphocholine).

200 g hexadecylphosphocholine, 80 g lactose, 50 g microcrystalline cellulose, 4 g talc, 5 g highly dispersed silicon dioxide and 10 g magnesium stearate were blended according to the process as described in Example 1. This filling mixture is filled in portions of 349 mg into gelatin hard capsules of 97 mg weight in a known way by using a suitable machine for encapsulation.

Each capsule as obtained has a total weight of 446 mg and contains 200 mg hexedecylphosphocholine. The ratio between hexadecylphosphocholine: flowability-controlling agent: fillers in the filling mixture is 1:0.095:0.65 (parts by weight)

Example 6

Hard Gelatine Capsule

Content: 250 mg miltefosine (hexadecylphosphocholine).

250 g hexadecylphosphocholine, 80 g lactose, 50 g microcrystalline cellulose, 5 g talc, 5 g highly dispersed silicon dioxide and 15 g magnesium stearate were blended according to the process as described in Example 1. This filling mixture is filled in portions of 405 mg into gelatin hard capsules of 97 mg weight in a known way by using a suitable encapsulation machine.

Each capsule as obtained has a total weight of 502 mg and contains 250 mg hexadecylphosphocholine. The ratio between hexedecylphosphocholine: flowability-controlling agent: fillers in the filling mixture is 1:0.1:0.52 (parts by weight).

Example 7

Tablets

Content: 250 mg of miltefosine (hexadecylphosphocholine).

50 g of hexadecylphosphocholine, 24.25 g of microcrystalline cellulose and 22.00 g of anhydrous dicalcium phosphate are sieved and blended. 3.75 g of magnesium stearate are sieved and added to the blend. Then the mixture is blended again. The resulting blend is compressed into tablets each weighing 500 mg. One tablet contains 250 mg hexedecylphosphocholine.

The ratio of miltefosine (hexadecylphosphocholine): flowability-controlling agent/surfactant: fillers in the tablet is 1:0.07:0.925 (parts by weight).

Example 8

Tablets

Content: 30 mg of miltefosine (hexadecylphosphocholine).

23 g of hexadecylphosphocholine, 23 g of microcrystalline cellulose, 52 g of spray dried lactose are sieved and blended. 1 g of colloidal silicon dioxide and 1 g of magnesium stearate are added. The mixture is then blended again.

The resulting blend is compressed into tablets each weighing 130.5 mg. One tablet contains 30 mg miltefosine (hexadecylphosphocholine).

The ratio of miltefosine (hexadecylphosphocholine): flowability-controlling agent/surfactant: fillers in the tablet is 1:0.087:0.31 (parts by weight).

Example 9

Effervescent Tablets and Blend

Content of miltefosine (hexadecylphosphocholine): 250 mg.

1700 g of granular sodium bicarbonate heated at 100° C. for 60 min in an oven. After cooling to room temperature the converted bicarbonate is mixed with 160 g of granular monobasic calcium phosphate, 1030 g of granular anhydrous citric acid, 100 g of talcum and 50 g of magnesium stearate. 300 g of hexedecylphosphocholine is added to the resulting mixtures, which is then blended for 10 minutes.

The resulting effervescent blend is compressed into tablets each weighing 278 mg.

One effervescent tablet contains 250 mg of hexadecylphosphocholine.

The ratio between miltefosine (hexadecylphosphocholine): flowability-controlling agent/surfactant fillers in the tablet is 1:0.50:0.53 (parts by weight).

Alternatively, the effervescent blend can be filled in an amount of 278 mg into sachets thus obtaining an effervescent blend.

Example 10

Effervescent Tablets and Blend

Content: 50 mg of miltefosine (hexadecylphosphocholine).

1600 g of granular sodium bicarbonate are heated at 100° C. for 60 min in an oven. After cooling to room temperature the converted bicarbonate is mixed with 150 g of granular monobasic calcium phosphate, 900 g of granular anhydrous citric acid, 80 g of talcum and 30 g of magnesium stearate. To the resulting mixture are added 200 g of miltefosine and blended for 10 minutes. The resulting mixture is compressed into tablets each weighing 740 mg. One effervescent tablet contains 50 mg of hexadecylphosphocholine.

The ratio between miltefosine (hexadecylphosphocholine): flowability-controlling agent/surfactant fillers in the tablet is 1:0.55:0.75 (parts by weight).

Alternatively, the effervescent blend can be filled in an amount of 740 mg into sachets thus obtaining an effervescent blend.

Example 11

Drinkable Blend (Sachets)

Content—50 mg of miltefosine (hexadecylphosphocholine).

5 g of miltefosine, 308 g of lactose, 280 g of microcrystalline cellulose, 5 g of saccharin and 2 g of colloidal silicon dioxide are blended. The blend is filled into sachets. One sachet weighs 6 g and contains 50 mg of miltefosine.

The ratio between miltefosine (hexadecylphosphocholine): flowability-controlling agent/surfactant: fillers in the blend is 1:0.4:117.5 (parts by weight).

Example 12

Drinkable Blend (Sachets)

Content: 100 mg of miltefosine (hexadecylphosphocholine).

10 g of miltefosine, 200 g of lactose, 250 g of microcrystalline cellulose, 7 g of saccharin and 3 g of colloidal silicon dioxide are blended. The blend is filled into sachets.

One sachet weighs 4.7 g and contains 100 mg of miltefosine.

The ratio of miltefosine (hexadecylphosphocholine): flowability-controlling agent/surfactant: fillers in the blend is 1:0.3:45 (parts by weight).

Example 13

Drinkable blend (Sachets) (content—200 mg of hexadecylphosphocholine).

20 g of miltefosine, 306 g of lactose, 403 g of microcrystalline cellulose, 5 g of saccharin and 6 g of colloidal silicon dioxide are blended. The blend is filled into sachets. One sachet weighs 7.4 g and contains 200 mg of miltefosine.

The ratio between miltefosine (hexadecylphosphocholine): flowability-controlling agent/surfactant fillers in the blend is 1:0.3:35.5 (parts by weight).

II. RESULTS OF CLINICAL STUDIES IN THE TREATMENT OF LEISHMANIASIS WHERE CAPSULES ACCORDING TO THE PRESENT INVENTION WERE ADMINISTERED PERORALLY

In the following, the abbreviations mean:
once qod=one administration every other day;
BID qod=two administrations every other day;
BID=two daily administrations;
TID=three daily administrations;
DID=four daily adminstrations;
Miltefosine (MILT, hexadecylphosphocholine, ASTA Medica), an antineoplastic alkylphospholipid, is active in experimental visceral leishmaniasis (VL). To test oral MILT in human VL, 30 male Indian patients from Bihar (age>14 years; 18 of the 30 were antimony (Sb) failures) with splenic aspirate-positive VL were treated in 6 groups of 5 patients each (Groups A–F) for 28 days with escalating doses by oral administration of capsules according to example 1: (A) 50 mg once qod (qod=quantity every other day), (B) 50 mg BID god (BID=twice per day), and then daily using 50 mg (C) BID (100 mg/d), (D) TID (150 mg/d), (E) QID (200 mg/d), and (F) 5×per day (250 mg/d).

16 patients were afebrile by day 7. Day 14 results in 30 patients: 25 afebrile, 25 decreased spleen size, 28 with negative spleenic aspirates (apparent parasitologic cure); 21 of 30 showed all 3 responses and were thus considered apparent cures. 1 Group F patient died on day 21 (drug stopped on day 19) with severe vomiting and diarrhea (possibly drug or intercurrent gastroenteritis-associated), dehydration, and renal failure. Mild vomiting or diarrhea lasting 3–7 days developed in most patients in Groups B–E.

1 patient in Group E and 3 more in. Group F were removed on days 7, 7, 8 and 10 because of vomiting. 200 mg/d was therefore the maximum tolerated daily dose.

There was no hematologic toxicity.

1 Group F patient developed increased hepatic transaminases (resolved).

On day 28, 29 of 29 patients (100%) were apparent cures including the 4 patients who received less than 10 days of therapy and were not further treated.

Within 6 months, 7 of 29 apparent cures relapsed (A-3/5, B-3/5, D-1/5); thus, 6 of 7 relapses were in the low-dose, qod-dosing groups (A, B). Within 6 months, apparent cure (no relapse, parasite-free bone marrow aspirate) has been achieved in 21 of 26 patients (A2/5, B-2/5, C-5/5, D-4/5, E5/5); 1 patient is still in follow up; 14 of the first 21 patients with definite cure had failed prior therapy with antimony.

These results demonstrate that the solid pharmaceutical compositions containing miltefosine and the dosage scheme according to the present invention are effective in the treatment of leishmaniasis by peroral administration. Apparent cures were even observed in patients with antimony-unresponsive visceral infection.

Modifications and other Embodiments

Various modifications and variations of the described process and concept of the invention will be apparent to those skilled in the art without departing from the scope and spirit of the invention. Although the invention has been described in connection with specific preferred embodiments, it should be understood that the invention as claimed is not intended to be limited to such specific embodiments. Various modifications of the described modes for carrying out the invention which are obvious to those skilled in the medical or pharmacological arts or related fields are intended to be within the scope of the following claims.

Incorporation by Reference

Each reference, patent application or patent publication cited by or referred to in this disclosure is incorporated by reference in its entirety. Any patent document to which this application claims priority is also incorporated by reference in its entirety. Specifically, PCT/EP98/00345, filed Jan. 22, 1998 is hereby incorporated by reference.

What is claimed is:

1. A method for the treatment of leishmaniasis in humans comprising:
oral administration of a solid pharmaceutical composition, which comprises:
hexadecylphosphocholine (miltefosine),
a flow-controlling agent and/or lubricant, and
a filler, wherein a total daily dosage in the range of about 10 to about 250 mg of the active ingredient (a.i.) hexadecylphosphocholine is administered orally over a period of time of about 2 to about 6 weeks and wherein said solid pharmaceutical composition is produced by a process that does not use chloroform and is thereby free from the risk of contamination with chloroform and suitable for use in humans.

2. The method of claim 1, wherein the total daily dosage is about 50 to about 150 mg of the a.i. hexadecylphosphocholine.

3. The method of claim 1, wherein administration is continued on a daily basis for a period of time of about up to 4 additional weeks.

4. The method of claim 1, wherein the oral administration takes place once, twice or thrice per day and the total dosage is about 50, about 100 and about 150 mg a.i. hexadecylphosphocholine, respectively.

5. The method of claim 4, wherein multiple daily doses are administered in about equal portions.

6. The method of claim 1, wherein the solid pharmaceutical composition is selected from the group consisting of capsules, tablets, effervescent tablets, effervescent blends and sachets or drinkable blends.

7. The method of claim 1, wherein the flow-controlling agent additionally includes a member selected from the group consisting of talc, magnesium stearate and mixtures thereof.

8. The method of claim 1, wherein the filler additionally includes a member selected from the group consisting of cellulose, mannitol, a calcium phosphate and mixtures thereof.

9. The method or claim 1, wherein the ratio between hexedecylphosphocholine ("HPC") and the flow-controlling agent and/or lubricant is about 1 part by weight of HPC and from about 0.01 to about 0.6 parts by weight of flow-controlling agent and/or lubricant.

10. The method of claim 1, wherein the ratio between hexedecylphosphocholine ("HPC") and the filler is about 7 parts by weight of HPC and from about 0.1 to about 120 parts by weight of filler.

11. The method of claim 1, wherein a solid pharmaceutical composition with sufficient flowability is obtained by, simple physical blending hexedecylphosphocholine, the flow-controlling agent and/or lubricant, and the filler.

12. The method of claim 1, wherein the solid pharmaceutical composition is granulated prior to processing into tablets, capsules or sachets.

13. The method of claim 1, wherein the solid pharmaceutical composition further comprises one or more excipients or auxiliary agents selected from the group consisting of one or more disintegrating agents, binders or binding agents, anti-adherent agents, carriers, diluents, effervescent mixtures when the composition is an effervescent tablet or effervescent blend, flavoring agents, sweeteners, and aromatic agents.

14. A method for the treatment of leishmaniasis in mammals other than humans by oral administration of a solid pharmaceutical composition comprising:

hexadecylphosphocholine (miltefosine), a flow-controlling agent and/or lubricant, and a filler, wherein a total daily dosage in the range of about 1 to about 15 mg active ingredient (a.i.) hexadecylphosphocholine per kg body weight of the mammal (mg a.i./kg) is administered over a period of time of about 2 to about 8 weeks, wherein said solid pharmaceutical composition is produced by a process that does not use chloroform and is thereby free from the risk of contamination with chloroform and suitable for use in mammals other than humans.

15. The method of claim 14, wherein the method of treatment comprises the administration of a loading dosage in the range of about 3 to about 15 mg a.i./kg, followed by the administration of a daily maintenance dosage in the range of about 1 to about 10 mg a.i./kg.

16. The method of claim 14, wherein the loading dosage is in the range of about 5 to about 10 mg a.i./kg.

17. The method of claim 14, wherein the maintenance dosage is in the range of about 3 to about 5 mg a.i./kg.

18. The method of claim 14, wherein the period of time for oral administration is about 4 weeks.

19. The method of claim 14, wherein said mammal is a pet or small companion animal.

20. A method for the treatment of leishmaniasis in mammals, comprising:

simultaneously or subsequently administering a solid pharmaceutical composition comprising:

hexadecylphosphocholine (miltefosine), a flow-controlling agent and/or lubricant, a filler, and an antiemeticum and/or antidiarrhoeal, wherein said antiemeticum and said antidiarrhoeal can be administered either together or independently of each other, wherein said solid pharmaceutical composition is produced by a process that does not use chloroform and is thereby free from the risk of contamination with chloroform and suitable for use in mammals.

21. The method of claim 1, wherein hexadecylphosphocholine (miltefosine) is blended with a flow-controlling agent and/or lubricant comprising silicon dioxide and a filler comprising lactose and cellulose.

22. The method of claim 14, wherein the hexadecylphosphocholine (miltefosine) is blended with a flow-controlling agent and/or lubricant comprising silicon dioxide and a filler comprising lactose and cellulose.

23. The method of claim 20, wherein the hexadecylphosphocholine (miltefosine) is blended with a flow-controlling agent and/or lubricant comprising silicon dioxide and a filler comprising lactose and cellulose.

* * * * *